US007262006B1

(12) United States Patent
Belly et al.

(10) Patent No.: US 7,262,006 B1

(45) Date of Patent: Aug. 28, 2007

(54) RAPID AND EFFICIENT CAPTURE OF DNA FROM SAMPLE WITHOUT USING CELL LYSING REAGENT

(75) Inventors: Robert T. Belly, Webster, NY (US); Jianbo Sun, Beijing (CN)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 10/019,514

(22) PCT Filed: May 1, 2000

(86) PCT No.: PCT/US00/11651

§ 371 (c)(1), (2), (4) Date: Feb. 21, 2003

(87) PCT Pub. No.: WO00/66783

PCT Pub. Date: Nov. 9, 2000

(51) Int. Cl.
*C12Q 1/68* (2006.01)

(52) U.S. Cl. .......................................................... 435/6

(58) Field of Classification Search .................... 435/6, 435/91.1, 91.2; 536/23.1

See application file for complete search history.

(56) References Cited

U.S. PATENT DOCUMENTS 4,089,747 A 5/1978 Bruschi
4,683,195 A 7/1987 Mullis et al.
4,683,202 A 7/1987 Mullis
4,713,326 A 12/1987 Dattagupta et al.
4,795,698 A 1/1989 Owen et al.
4,889,818 A 12/1989 Gelfand et al.
4,914,210 A 4/1990 Levenson et al.
4,920,061 A 4/1990 Poynton et al.
4,962,029 A 10/1990 Levenson et al.
4,965,188 A 10/1990 Mullis et al.
4,994,373 A 2/1991 Stavrianopoulos et al.
4,997,772 A 3/1991 Sutton et al.
5,118,801 A 6/1992 Lizardi et al.
5,147,777 A 9/1992 Sutton et al.
5,155,166 A 10/1992 Danielson et al.
5,173,260 A 12/1992 Zander et al.
5,229,297 A 7/1993 Schnipelsky et al.
5,231,015 A 7/1993 Cummins et al.
5,312,728 A 5/1994 Lizardi et al.
5,334,499 A 8/1994 Burdick et al.
5,338,671 A 8/1994 Scalice et al.
5,380,489 A 1/1995 Sutton et al.
5,434,270 A 7/1995 Ponticello et al.
5,523,368 A 6/1996 Ponticello et al.
5,582,988 A * 12/1996 Backus et al. ................. 435/6
5,587,287 A 12/1996 Scalice et al.
5,622,822 A 4/1997 Ekeze et al.
5,683,877 A 11/1997 Lu-Chang et al.
5,702,884 A 12/1997 Ekeze et al.
5,925,517 A 7/1999 Tyagi et al.

FOREIGN PATENT DOCUMENTS

EP H-0 070 687 1/1983
EP A-0 308 236 3/1989
EP A-0 320 308 6/1989
EP A-0 393 744 10/1990
EP A-0 428 197 5/1991
EP A-0 439 182 7/1991
EP A-0 439 222 7/1991
EP A-0 487 218 5/1992
EP A-0 512 334 11/1992
EP A-0 408 738 1/1994
EP A-0 707 077 9/1995
EP 0 953 635 A1 11/1999
EP 0 871 767 B1 3/2002
GB A-2 327 497 1/1999
WO WO89/06691 7/1989
WO WO91/12342 8/1991
WO WO92/16659 10/1992
WO WO95/16792 6/1995
WO WO96/15262 5/1996
WO WO96/32500 10/1996
WO WO97/34015 9/1997
WO WO99/004037 A1 1/1999
WO WO 01/49877 A1 7/2001

OTHER PUBLICATIONS

Gwynne et al., "Drug Discovery and Biotechnology Trends Genomes and Microbes: Resisting Drug Resistance," online publication from www.sciencemag.org, publication date, May 9, 2003, pp. 1-8 (print out).*

(Continued)

*Primary Examiner*—Young J. Kim
(74) *Attorney, Agent, or Firm*—Catherine K. Gowen

(57) ABSTRACT

Nucleic acids can be made available for amplification or other treatment after admixture of a sample with specific weakly basic polymers to form a precipitate with the nucleic acids at acidic pH. After removing non-precipitated materials, the pH is then made basic, thereby releasing the nucleic acids from the polymer. This method for preparing specimen samples is simple and quite rapid, and the released nucleic acids can be further treated in hybridization assays or amplification procedures. No surfactant or other cell lysing reagents are employed. The weakly basic polymers are water-soluble and cationic at acidic pH, but neutral in charge at basic pH.

6 Claims, 2 Drawing Sheets

OTHER PUBLICATIONS

Manen e tal., "A fully automatable enzymatic method for DNA extraction from plant tissues," BMC Plant Biology, vol. 5, No. 23, pp. 1-9.*
Steinman, C.R., J. Clin. Invest. 56: 512-515, 1975.4.
Raptis, L. et al., J. Clin. Invest. 66:1391-1399, 1980.
Leon, S. A., et al., Cancer Res., 37: 646-650, 1977.
Stroun, M., et al., Eur. J. Cancer Clin. Oncol.28: 707-712, 1987.
Fournie, G. J., et al., Cancer Lett., 91: 221-227, 1995.
Lin, A., et al., BioTechniques 24: (6) 937-940, 1998.
Sorenson, G. D., et al., Cancer Epidemiology, Biomakers and Prevention 3:67-71., 1994.
Vasyukhin, V., et al., *In* Challenges of Modern Medicine, vol. 5, Biotechnology Today R. Verna, and A. Shamoo, Eds, 141-150. Aera-Serono Symposia Publications, Rome.
Mulcahy, H. E., et al., Clin. Cancer Res., 4: 271-275., 1998.
Kopreski, M. S., et al., Brit. J. Cancer 76: 1293-1299, 1997.
Chen, X., et al., Nature Medicine 2: 1033-1035, 1996.
Vasioukin, V., et al., Brit. J. Haematology 86: 774-779, 1994.
Tada, M., et al., Cancer Res. 53: 2472-2474, 1993.
Lo Dennis, Y.M., et al., Am. J. Human Genet. 62: 768-775, 1998.
Laure, et al., The Lancet, pp. 538-540 (Sep. 3, 1988).
Maniatis, et al., Molecular Cloning: A Laboratory Manual, pp. 280-281 (1982).
Gross-Belland, et al., Eur. J. Biochem., 36,32 (1973).
Agrawal, et al., Nucleic Acid Res., 14, pp. 6227-45 (1986).
Anker, et al., Gastroenterology, 1997, vol. 112, No. 4, pp. 1114-1116.
Ferguson, W. J., et al., Analytical Biochemistry, 104, pp. 300-310 (1980).
Good, N. E., et al., Biochemistry, vol. 5., No. 2, pp. 467-477, Feb. 1966.
Good, N. E., and Izawa, S., Meth. Enzymol, 24, Part B. 53-68 (1972).
Supplementary Partial European Search Report, dated Mar. 5, 2004, for European Appln. No. EP 01 97 7871.
Sokol, Deborah L. et al., "Real Time Detection fo DNA-RNA Hybridization in Living Cells", Proc. Nat'l. Acad. Sci., USA, vol. 95, pp. 11538-11543, Sep. 1998.
A;Hnen, D. J. , et al., Kl-*ras* Mutation and p53 Overexpression Predict the Clinical Behavior of Colorectal Cancer: A Southwest Oncology Group Study.
Andreyev, H.J., et al., "Kirsten ras Mutations in Patients with Colorectal Cancer: the Multicenter "RASCAL" Study", Natl. Cancer Inst., (1998), 90(9), 675-684.
Aoki, T., et al., "*APC* and *p53* Mutations in de Novo Colorectal Adenocarcinomas", Hum. Mutat., (1994), 3(4):342-346.
Bos, J. L., et al., "Three Different Mutations in Codon 61 of the Human N-*ras* Gene Detected by Synthetic Oligonucleotide Hybridization", Nuclic Acids Res., (1984), 12(23):9155-9163.
Bos, J. L. et al., "Prevalence of *ras* Gene Mutations in Human colorectal Cancers", Nature (1987), 327(6120):293-297.
Bos, J. L. et al., "*Res* Oncogenes in Hematopoietic Malignancies", Hematol. Pathol., (1988), 2:55-63.
Bos, J. L., "The *ras* Gene Family and Human Carcinogenesis", Mutat. Res., (1988), 195:255-271.
Bos, J. L., "*ras* Oncogenes in Human Cancer: A Review", Can. Res., (1989), 49:4682-4689.
Calaluce, R., et al., "Micrometastasis in Colorectal Carcinoma: A Review", J. Surg. Oncol., (1998), 67:194-202.
Capon, D. J., et al., "Activation of Kl-*ras* 2 Gene in Human Colon and Lung Carcinomas By Two Different Point Mutations", Nature, (1983), 302:33-37.
Castells, Antoni, et al., "K-*ras* Mutations in DNA Extracted From the Plasma of Patients with Pancreatic Carcinoma: Diagnostic Utility and Prognostic Significance", Journal of Clinical Oncology (1999), 17(2), 578-584.
Cohen, J. B., et al., "A Point Mutation in the Last Intron Responsible for Increased Expression and Transforming Activity of the c-Ha-*ras* Oncogene", Nature, (1988), 334(6178):119-124.
Dukes, C. E., "The Cliaffication of Cancer of the Rectum", J. Pathol. Bacteriol., (1932), 35:323-332.
Findlay, J. B., et al., "Automated Closed-Vessel System for In Vitro Diagnostics Based on Polymerase Chain Reaction", Clin. Chem., (1993), 39(9):1927-1933.
Fuery, C. J., et al., "Detection of Rare Mutant Alleles by Restriction Endonuclease-Mediated Selective-PCR: Assay Design and Optimization", Clin. Chem., (2000), 46(5):620-624.
Haliassos, A., et al., "H-*ras* Oncogene Mutations in the Urine of Patients with Bladder Tumors: Description of Non-Invasive Method for the Detection of Neoplasia", Int. J. Oncol., (1992), 1:731-734.
Hayashi, N et al., "Generic Diagnosis Identifies Occult Lymph Node Metastases Undetectable by the Histopathological Method", Cancer Res., (1994), 54:3853-3856.
Hayashi, N., et al., "Genetic Diagnosis of Lymph-Node Metastasis in Colorectal Cancer", Lancet, (1995), 345:1257-1259.
Maebo, A., "Plasma DNA Level as a Tumor Marker In Primary Lung Cancer", Nihon Kyobu Shikkan Gakkai Zasshi, (1990), 28(8), 1085-91.
Moertel, C. G., et al., "Levamisole and Fluorouracil for Adjuvant Therapy of Resected Colon Carcinoma", Clin. Cancer Res., (1990), 322:352-358.
Nakamori, S., et al., "Genetic Detection of colorectal Cancer Cells in Cirulation and Lymph Nodes", Diz. Colon Rectum, •(1997), 40 (Suppl 10):S29-36.
Neri, a., et al., "Analysis of *RAS* Oncogene Mutations in Human Lymphoid Malignancies", Proc. Natl. Acad. Sci. USA, (1988), 85:9268-9272.
Puig, P., et al., "A Highly Sensitive Method for K-*ras* Mutation Detection is Useful in Diagnosis of Gastrointestinal Cancer", Int. J. Cancer, (2000), 85:73-77.
Roberts, N. J. et al., "Rapid, Sensitive Detection of Mutant jAlleles in Codon 12 of K-*ras* by REMS-PCR", BioTechniques, (1999), 27(3):418-422.
Rochlitz, C. F., et al., "Laboratory Methods, Use of the Polymerase Chain Reaction Technique to Create Base-Specific *ras* Oncogene Mutations", DNA, (1988), 7:515-519.
Saito, S., et al., "Screening of H-*ras* Gene Point Mutations in 50 Cases of Bladder Carcinoma", Int. J. Urol. (1997), 4:178-185.
Sanchez-Cespedes, M., et al., "Molecular Detection of neoplastic Cells in Lymph Nodes of Metastatic Colorectal Cancer Patients Predicts Recurrence", Clin. Cancer Res., (1999), 5:2450-2454.
Theillet, C., et al., Loss of a c-H-*ras*-1 Allele and Aggressive Human Primary Breast Carcinomas, Cancer Res., (1986), 46:4776-4781.
Turnbull, R. B., et al., "Cancer of the Colon: The Influence of the *No-Touch Isolation* Technic on Survival Rates", Ann. Surg., (1967), 166:420-427.
Tyagi, S., et al., "Molecular Beacons: Probes that Fluoresce Upon Hybridization", Nature Biotechnol., (1996), 14:303-308.
Tyagi, S., et al., "Multicolor Molecular Beacons for Allele Discrimination", Nature Biotechnol., (1998), 16:49-53.
Vogelstein, B., et al., "Genetic Alterations During Colorectal-Tumor Development", New England J. Med., (1988), 319(9), 525-532.
Ward, R., et al., "Restriction Endonuclease-Mediated Selective Polymerase Chain Reaction", Am. J. Pathol., (1998). 153:373-379.
PCT Int'l. Search Report, dated Nov. 5, 2003, for PCT Appln. No. PCT/US01/42422.
Search Report PCT/US/00/11651, dated May 14, 2001.

* cited by examiner

Standard Curve for DNA as Evaluated by TaqMan Amplification
with the β-actin Gene after 40 PCR cycles
Standard Curve - 112398
Unknowns
Standards
Slope: -4.786
Y-Intercept: 28.827
Correlation Coeff: 0.998
Threshold Cycle (Ct)
30.00
28.00
26.00
24.00
22.00
20.00
18.00
1.2ng
3ng
6ng
12ng
10 ^ 1
10 ^ 2
Starting Quantity

SEQUENCE LISTING

<160> NUMBER OF SEQ ID NOS: 6

<210> SEQ ID NO 1
<211> LENGTH: 28
<212> TYPE: DNA
<213> ORGANISM: HUMAN

<400> SEQUENCE: 1
tgaatataaa cttgtggtac ctggagct 28

<210> SEQ ID NO 2
<211> LENGTH: 28
<212> TYPE: DNA
<213> ORGANISM: HUMAN

<400> SEQUENCE: 2
atataaactt gtggtagttc cagctggt 28

<210> SEQ ID NO 3
<211> LENGTH: 26
<212> TYPE: DNA
<213> ORGANISM: HUMAN

<400> SEQUENCE: 3
gaattagctg tatcgtcaag gcactc 26

<210> SEQ ID NO 4
<211> LENGTH: 21
<212> TYPE: DNA
<213> ORGANISM: HUMAN

<400> SEQUENCE: 4
tcagcaaaga caagacaggt a 21

<210> SEQ ID NO 5
<211> LENGTH: 26
<212> TYPE: DNA
<213> ORGANISM: HUMAN

-continued

```
<400> SEQUENCE: 5

tatagatggt gaaacctgtt tgttgg                                          26


<210> SEQ ID NO 6
<211> LENGTH: 29
<212> TYPE: DNA
<213> ORGANISM: HUMAN

<400> SEQUENCE: 6

cttgctatta ttgatggcaa ccacacaga                                       29
```

RAPID AND EFFICIENT CAPTURE OF DNA FROM SAMPLE WITHOUT USING CELL LYSING REAGENT

FIELD OF THE INVENTION

This invention relates to a method for preparing a sample by capture and selective release of nucleic acids for detection. In particular, it relates to a method for capture and release of nucleic acids for subsequent treatment such as amplification. It also relates to a test kit for use in the method.

BACKGROUND OF THE INVENTION

Technology to detect minute quantities of nucleic acids has advanced rapidly over the last two decades including the development of highly sophisticated amplification techniques such as polymerase chain reaction (PCR). Researchers have readily recognized the value of such technology to detect nucleic acids which are indicative of diseases and genetic features in human or animal test specimens. The use of probes and primers in such technology is based upon the concept of complementarity, that is, the bonding of two strands of a nucleic acid by hydrogen bonds between complementary nucleotides (also known as nucleotide pairs).

PCR is a significant advance in the art to allow detection of very small concentrations of a targeted nucleic acid. The details of PCR are described, for example, in U.S. Pat. No. 4,683,195 (Mullis et al), U.S. Pat. No. 4,683,202 (Mullis) and U.S. Pat. No. 4,965,188 (Mullis et al), although there is a rapidly expanding volume of literature in this field.

In order to effectively amplify and detect a target nucleic acid, it is usually necessary to isolate that nucleic acid from cellular and other specimen debris. Various lysing procedures are known, including freezing, treatment with digesting enzyme such as proteases (for example, Proteinase K), boiling, and use of various detergents (see for example U.S. Ser. No. 178,202, filed Apr. 6, 1988 by Higuchi, and EP-A-0 428 197, published May 22, 1991), solvent precipitations and heating protocols.

Circulating DNA has been detected in blood serum and plasma. Nanogram quantities are detected in normal subjects (Steinman, C. R., J Clin. Invest. 56:512-515, 1975 and Raptis, L., et al., J. Clin. Invest. 66:1391-1399, 1980), and increased levels are detected in chronic autoimmune diseases (Leon, S. A., et al., Cancer Res., 37:646-650, 1977) and in cancer patients (Stroun, M., et al., Eur. J. Cancer Clin. Oncol. 28:707-712, 1987; Maebo, A., Jpn. J. Thorac. Dis. 28:1085-1091, 1990; Fournie, G. J., et al., Cancer Lett., 91:221-227, 1995; Lin, A., et al., BioTechniques 24:(6) 937-940, 1998; and Sorenson, G. D., et l., Cancer Epidemiology, Biomarkers and Prevention 3:67-71., 1994). Recently, it has become evident that free extracellular DNA present in blood serum and plasma can be used for genotype analysis (Lin, A., et al., BioTechniques 24:(6) 937-940, 1998), for detection of cancer (Mulcahy, H. E., et al., Clin. Cancer Res. 4:271-275, 1998), and DNA in maternal serum may be used in prenatal diagnostics (Lo Dennis, et al., Am. J. Human Genet. 62:768-775, 1998). Mutations present in a primary tumor, often can be detected using DNA from blood plasma or serum DNA (Sorenson, G. D., et al., Cancer Epidemiology, Biomarkers and Prevention 3:67-71., 1994; Vasyukhin, V., et al., In Challenges of Modern Medicine, Vol. 5, Biotechnology Today, R. Verna, and A. Shamoo, eds, 141-150. Aera-Serono Symposia Publications, Rome; Mulcahy, H. E., et al., supra.; Kopreski, M. S., et al., Brit. J. Cancer 76:1293-1299, 1997; Chen, X., et al. Nature Medicine 2: 1033-1035, 1996; Vasioukin, V., et al., Brit. J. Haematology 86:774-779, 1994; and Tada, M., et al., Cancer Res. 53:2472-2474, 1993). Thus, DNA present in serum and plasma represents a minimally invasive source for information related to cancer diagnosis, prognosis, and therapy.

To effectively amplify and detect a target nucleic acid, it is usually necessary to separate the nucleic acid from interfering substances present in a specimen of interest. Several different approaches have been used to concentrate and purify DNA from blood serum or plasma. Many of these methods involve multiple steps including phenol, ether, and chloroform treatment, dialysis, passage through Concanavalin A-Sepharose to remove polysaccharides and then centrifugation in a cesium chloride gradient (Vasyukhin, V., et al., supra.). More recently, Qiagen has commercialized a system for DNA concentration and purification based on a spin column protocol. The Quiagen protocol is complex, involving a total of eight steps, treatment with a protease, incubations at 70° C., and requires the use of at least 3 different buffers, in addition to a silica spin column centrifugation step.

Recently, Goecke et al. (WO 97/34015) reported the detection of extracellular tumor-associated nucleic acid in blood plasma and serum using nucleic acid amplification assays. In their preferred method, DNA is co-precipitated from plasma and serum using a multistep protocol involving an initial co-precipitation by gelatin, followed by solvent treatment and centrifugation. Other time-consuming and complex protocols involving the use of glass beads, silica particles or diatomaceous earth for extraction of DNA from serum and plasma are also described.

The use of weakly basic polymers for the capture and selective release of nucleic acids has been described U.S. Pat. No. 5,622,822 (Ekeze et al.), U.S. Pat. No. 5,582,988 (Backus et al.), and U.S. Pat. No. 5,434,270 (Ponticello, et al.). The protocols described in the aforementioned patents depend upon the use of a cell lysing agent or a cell lysing step. Surfactants are often used as cell lysing agents. The use of surfactants and other lysing agents results in the release of nucleic acids from cells and cellular components in blood; causing a large concentration of background DNA.

SUMMARY OF THE INVENTION

The problems associated with the use of lysing agents or lysing steps in prior art methods have been overcome with the method of the present invention.

The method of this invention involves the use of a weakly basic polymer, as described in the above-indicated US patents, for the capture and selective release of the captured nucleic acids from the polymer, but without the use of a lysing step or lysing agent, as performed using prior art methods.

According to one aspect of the invention, a simplified, easy-to-use method for recovering DNA from blood serum and plasma is provided. The method includes the use of a weakly basic polymer for binding DNA from a sample such as blood serum or plasma. Upon binding DNA, the polymer becomes insoluble. The polymer-bound DNA is then separated from the liquid mixture which comprises non-desirable soluble substances. DNA is then released from the polymer by means of alkali addition. Thus the method of the present invention requires only three steps: (a) contact of sample with buffer, (b) contact and incubation of mixture formed in step (a) with a weakly basic polymer, and (c) release of the DNA bound to polymer in step (b) by contact with alkali. The method eliminates the need for extraction with alcohol or other solvent and toxic materials such as phenol or chloroform, and lysing agents are not used. The method not only simplifies DNA recovery, but also results in an improvement in yield of amplifiable target DNA. Although the method is preferably used with serum and blood as the sample, it is applicable to other body fluids including but not limited to urine, bile, spinal fluid, bronchial lavage (BAL), colonic washes, and stool. In addition, samples of any type can be used, including those collected from animals, humans, environmental and microbial specimens.

In another aspect the present invention relates to amplification and detection of target DNA using the method of DNA recovery described hereinabove.

The inventive methods of the invention comprise the steps of:

A) at a pH of less than 7, contacting a sample suspected of containing a nucleic acid with a water-soluble, weakly basic polymer in an amount sufficient to form a water-insoluble precipitate of the weakly basic polymer with all nucleic acids present in the sample, B) separating the water-insoluble precipitate from the sample, and C) contacting the precipitate with a base to raise the solution pH to greater than 7, and thereby releasing the nucleic acids from the weakly basic polymer, the weakly basic polymer comprising recurring units derived by addition polymerization of one or more ethylenically unsaturated polymerizable monomers having an amine group which can be protonated at acidic pH.

This invention also provides a method for the amplification and detection of a target nucleic acid comprising:

I) providing a target nucleic acid using the steps of:

A) at a pH of less than 7, contacting a sample suspected of containing a target nucleic acid with a water-soluble, weakly basic polymer in an amount sufficient to form a water-insoluble precipitate of the weakly basic polymer with all nucleic acids present in the sample, including the target nucleic acid, B) separating the water-insoluble precipitate from the sample, and C) contacting the precipitate with a base to raise the solution pH to greater than 7, and thereby releasing the nucleic acids, including the target nucleic acid, from the weakly basic polymer, the weakly basic polymer comprising recurring units derived by addition polymerization of one or more ethylenically unsaturated polymerizable monomers having an amine group which can be protonated at acidic pH, II) amplifying the target nucleic acid present among the released nucleic acids, and III) detecting the amplified target nucleic acid.

A test kit for amplification of a target nucleic acid comprises, separately packaged:

a) an amplification reaction mixture comprising one or more amplification reagents, and b) a weakly basic polymer comprising recurring units derived by addition polymerization of one or more ethylenically unsaturated polymerizable monomers having an amine group which can be protonated at acidic pH.

The present invention provides a rapid, simple and effective method for selectively isolating and providing nucleic acids for further treatment, such as hybridization assays or amplification procedures. This invention overcomes the problems noted above relating to conventional isolation means, including the use of polyethyleneimine. In addition, the problems presented by the use of polyethyleneimine combined with a fluorinated phosphate surfactant are also avoided because the surfactant is not needed. The sample preparation method of this invention is not tedious and requires a minimum of steps, thereby making it more readily automated. It usually can be carried out within about 15 minutes (preferably within 10 minutes).

These advantages are provided by using in place of the polyethyleneimine a "weakly basic" polymer which is cationic and water-soluble at acidic pH, but deprotonates at a basic pH which is significantly above the pKa of the polymer. By "weakly basic" is meant that the polymer pKa is less than 7, and more likely less than 6.5. Thus, the polymer can be used at low pH to precipitate nucleic acids because of the ionic interaction of the cationic polymer and the anionic phosphate backbone of nucleic acids.

After removing noncomplexed materials, and upon a pH adjustment to basic conditions, the nucleic acids are released (or decomplexed) from the weakly basic polymer of the precipitate and available for further treatment, such as amplification. The amplification procedures can be carried out under basic conditions.

DETAILED DESCRIPTION OF THE INVENTION

Figure 1:
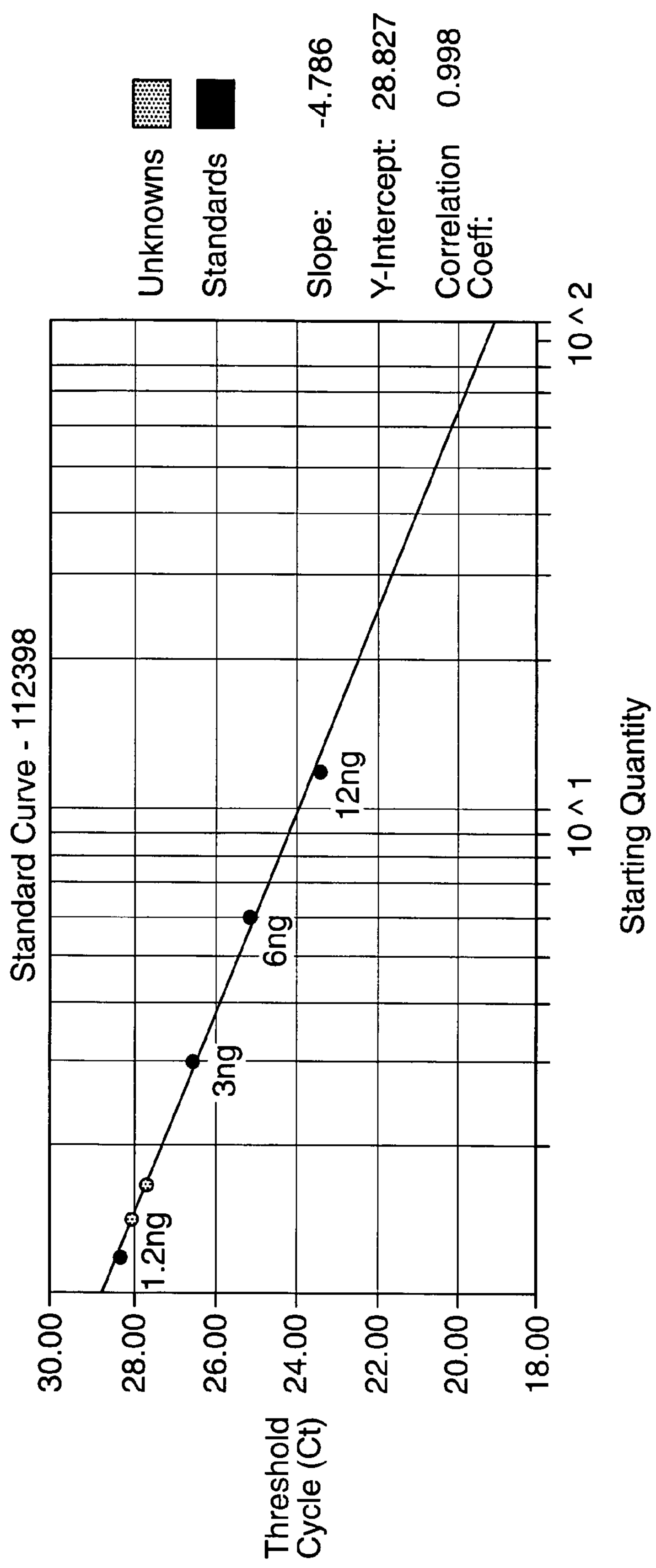
FIG. 1 illustrates a standard curve for DNA as evaluated by TaqMan amplification with the β-actin gene after 40 PCR cycles.
Figure 2:
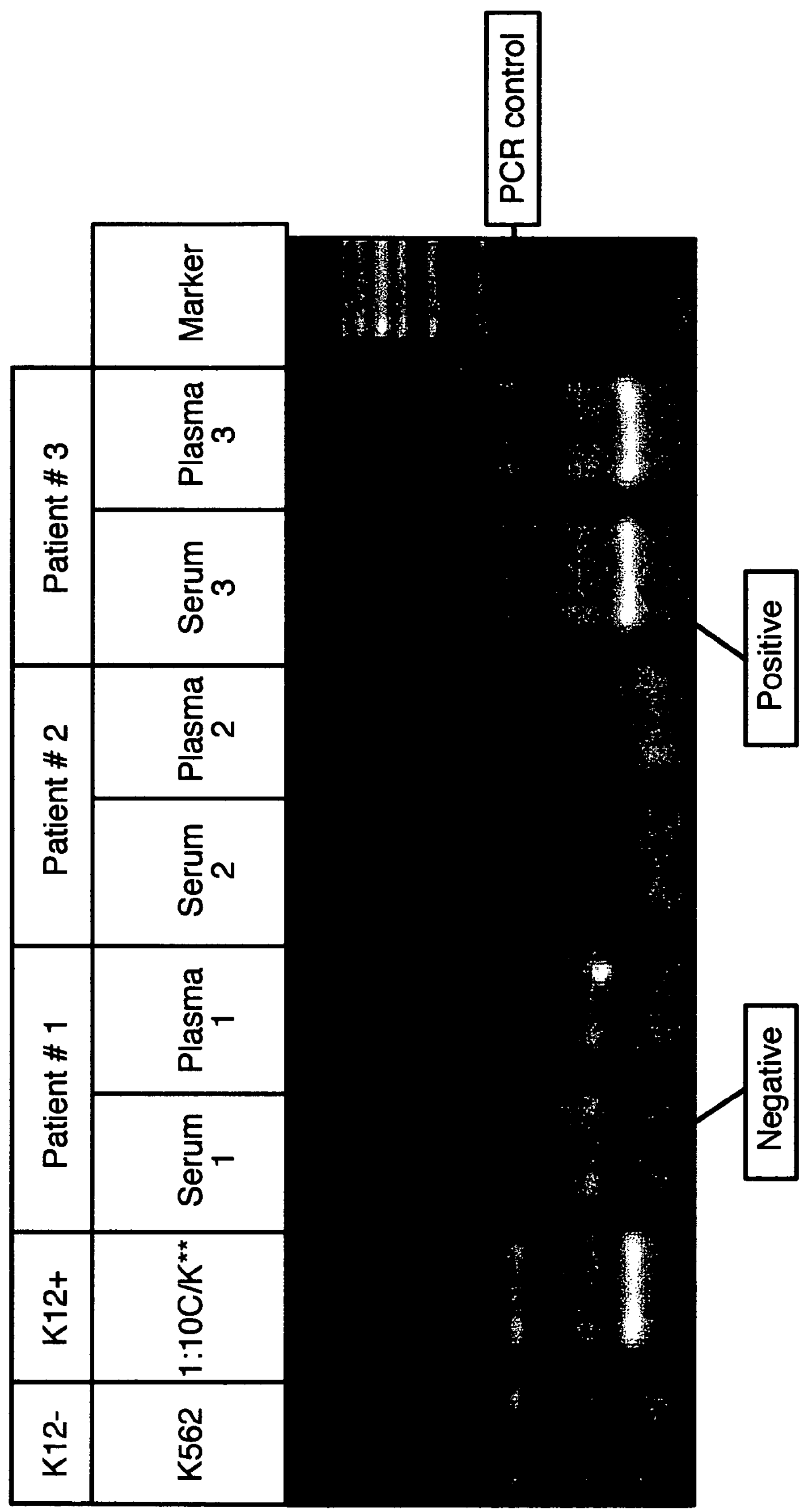
FIG. 2 ILLUSTRATES THE RESULTS OF ANALYSIS FOR A k-12 ras muttion as determined by gel electrophoresis after REMS-PCR in accordance with Example 7.

The present invention is especially suited for the extraction and detection of one or more target nucleic acids present in a sample of any type collected from animals, humans, environmental or microbial specimens. The nucleic acids so obtained can be further treated by subjecting them to conventional hybridization assays, the procedures of which are well known in the art (for example, U.S. Pat. No. 4,994,373, incorporated herein by reference with respect to the hybridization technology).

However, for the sake of brevity, the remaining discussion will be directed to preferred embodiments whereby the nucleic acids are subjected to amplification procedures, particularly PCR. However, the scope of this invention is not intended to be so limited because other amplification techniques (such as LCR) can be used also.

The general principles and conditions for amplification and detection of nucleic acids using polymerase chain reaction are quite well known, the details of which are provided in numerous references including U.S. Pat. No. 4,683,195 (Mullis et al), U.S. Pat. No. 4,683,202 (Mullis), U.S. Pat. No. 4,965,188 (Mullis et al) and WO-A-91/12342. The noted U.S. patents are incorporated herein by reference. In view of the teaching in the art and the specific teaching provided herein, a worker skilled in the art should have no difficulty in practicing the present invention by combining the preparatory method of this invention with polymerase chain reaction procedures, or with any other amplification procedure known in the art.

Other amplification procedures which can be used in the practice of this invention include, but are not limited to, ligase chain reaction as described, for example, in EP-A-0 320 308 (published December, 1987) and EP-A-0 439 182 (published January, 1990).

Test specimens ("samples") can include body fluids or other materials containing genetic DNA or RNA. The target nucleic acid can be extracted from any suitable human, animal, microbial, viral or plant source.

The advancement disclosed herein contemplates that prior to contact with the weakly basic polymer defined herein, no extraction of nucleic acids from the specimen is required. While the prior art teaches various lysing procedures known in the art (including those described by Laure et al in The Lancet, pp. 538-540 (Sep. 3, 1988), Maniatis et al, Molecular Cloning: A Laboratory Manual, pp. 280-281 (1982), Gross-Belland et al in Eur. J. Biochem., 36, 32 (1973) and U.S. Pat. No. 4,965,188 (noted above)). Extraction of DNA from whole blood or components thereof is described, for example, in EP-A-0 393 744 (published Oct. 24, 1990), U.S. Pat. No. 5,231,015 (Cummins et al) and U.S. Pat. No. 5,334,499 (Burdick et al); the lysing procedure being dependent upon the type of specimen being used as the source of nucleic acids; a preferred lysing procedure includes heating the specimen in the presence of a suitable nonionic surfactant, a number of which are well known in the art. Another useful lysing procedure is described in U.S. Ser. No. 08/063, 169 (filed May 18, 1993 by Ekeze and Kerschner) whereby a whole blood specimen is mixed with a buffered solution of ammonium chloride, followed by additional steps which includes a second mixing with ammonium chloride, the methods of the instant invention do not employ a lysing step.

The sample, first diluted and admixed with a buffer at below pH of about 7.0, is admixed with a weakly basic polymer (defined below) in an amount sufficient to complex with all nucleic acids present in the sample, forming a water-insoluble precipitate. This polymer is water-soluble at acidic pH. Generally, the amount of polymer present is at least about 0.01 weight percent, with from about 0.05 to about 0.5 weight percent preferred. Of course, a skilled artisan would know how to adjust the amount of polymer to accommodate any quantity of nucleic acids. Mixing can be carried out in any suitable manner for up to 30 minutes (generally less than 5 minutes) and at any suitable temperature (generally from 15° to 35° C.

Suitable buffers for admixture with sample include those buffers having a pKa less than 7, more preferably less than pKa 6.5, including MES (2-[N-Morpholino]ethanesulfonic acid) at pK 6.1, BIS-TRIS (bis[2-Hydroxyethyl]iminotris [hydroxymethyl]methane; 2-bis[2-hydroxyethyl]amino-2-[hydroxymethyl]-1,3-propanediol) at pK 6.5, ADA (N-[2-Acetamido]-2-iminodiacetic acid; N-[Carbamoylmethyl] iminodiacetic acid) at pK 6.6, ACES (N-[Carbamoylmethyl]-2-aminoethanesulfonic acid; N-[2-Acetamido]-2-aminoethanesulfonic acid) at pK 6.8, PIPES (piperazine-N,n'-bis[2-ethanesulfcid]; 1,4-piperazinediethanesulfonic acid) at pK 6.8, MOPSO (3-[N-Morpholino]-2-hydroxypropanesulfonic acid) at pK 6.9, BIS-TRIS Propane (1,3-bis[tris(Hydroxymethyl)methylamino]propane) at pK 6.8, PBS (phosphate buffered saline), and TRIS (tris (hydroxymethyl)aminomethane), the weakly basic polymer can be used in its water-soluble free form, or attached to a water-insoluble substrate, such as in an affinity column, or attached to polymeric, glass or other inorganic particles. Thus, the polymers can be attached using conventional means (for example, absorption, covalent bonds or specific binding reactions) to a suitable substrate, including glass, polymeric or magnetic particles, filters or films. Where the weakly basic polymer is water-insoluble even at basic pH, it can be removed through filtration, centrifugation or other conventional means after the nucleic acids are released.

While bound to the weakly basic polymer, however, the nucleic acids are not useful. It is then necessary to separate the water-insoluble precipitate from the remainder of the sample which may contain considerable cellular debris and excess polymer. This separation can be achieved using any of various conventional procedures, including centrifugation or filtration after which the liquid is discarded. Centrifugation is preferred in the practice of this invention and can be carried out at greater than about 1,000×g, for one minute to 5 minutes.

After the separation step, the nucleic acids can be decomplexed or released from the weakly basic polymer, by contacting the precipitate with a base, with or without heating. Strong bases may be used without heating, and they include, but are not limited to, sodium hydroxide, potassium hydroxide, ammonium hydroxide, lithium hydroxide, sodium carbonate, sodium bicarbonate, a tertiary amine (such as triethylamine, diisopropylethylamine and lutidine), tricine, bicine or any other organic or inorganic base which would be readily apparent to one skilled in the art. Useful weaker bases may include basic buffers such as tris(hydroxymethyl)aminomethane (or acid addition salts thereof), N,N-bis(2-hydroxyethyl)glycine, N-tris(hydroxymethyl) methyl-glycine, and others well known in the art. Heating may be necessary when weaker bases are used.

Such heating can be carried out for up to 15 minutes (generally less than 5 minutes) at a temperature that is at least about 50° C., and preferably is from about 95° to about 125° C., under suitable pressure. As used in this paragraph, "about" refers to

+/−0.5° C.

In preferred embodiments, weaker bases can be used with heating, to release the nucleic acids from the precipitate. This provides a solution containing nucleic acids which are ready for amplification without further treatment. Such weaker bases may be buffers, such as tris(hydroxymethyl) aminomethane hydrochloride.

In some embodiments, the polymers used in such embodiments are those (defined below) which are water-insoluble even at basic pH. Such polymers can be removed from the system after release of nucleic acids and prior to amplification if desired.

The resulting solution containing released nucleic acids has a basic pH. In some instances, the nucleic acids can be further treated without any further adjustment in pH. In other embodiments where a strong base is used, the pH of the solution may be adjusted (generally downward) to from about 6 to about 9 (preferably from about 7.5 to about 9), using any suitable acid or buffer, such as tris(hydroxymethyl)aminomethane hydrochloride, N,N-bis(2-hydroxyethyl)glycine, N-tris(hydroxymethyl)methylglycine and others which would be readily apparent to one skilled in the art. The amounts of such materials needed to achieve the desired pH would be readily apparent to one skilled in the art.

At basic pH, the polymer used for capture of nucleic acids can be either water-soluble or water-insoluble, and monomers needed for providing such properties are described below.

The described method of capturing and releasing nucleic acids of this invention is typically carried out within about 20 minutes, and preferably within about 10 minutes.

As used herein, unless otherwise noted, the modifier "about" refers to a variance of 110% of the noted values. When used with pH values, "about" refers to +/−0.5 pH unit.

In a preferred embodiment of this invention, a method for the amplification and detection of a target nucleic acid comprises:

I) providing a sample suspected of containing a target nucleic acid,

II) subjecting the target nucleic acid to the steps of:

A) at a pH of less than 7, contacting the target nucleic acid with a water-soluble, weakly basic polymer in an amount sufficient to form a water-insoluble precipitate of the weakly basic polymer with all nucleic acids present in the sample, including the target nucleic acid, B) separating the water-insoluble precipitate from the sample, and C) contacting the precipitate with a base to raise the solution pH to greater than 7, and thereby releasing the nucleic acids, including the target nucleic acid, from the weakly basic polymer, the weakly basic polymer comprising recurring units derived by addition polymerization of one or more ethylenically unsaturated polymerizable monomers having an amine group which can be protonated at acidic pH, III) without further adjustment of pH, amplifying the released target nucleic acid, and V) detecting the amplified target nucleic acid.

In the foregoing method, it is still more preferred that the weakly basic polymer is water-insoluble at basic pH, and the method further comprises the step of removing the water-insoluble polymer after release of the target nucleic acid but prior to amplification thereof.

The weakly basic polymer used in the practice of this invention is prepared from one or more ethylenically unsaturated polymerizable monomers, at least one of which has an amine group which can be protonated at acidic pH. Thus, at acidic pH, the polymer is protonated to form the acid addition salt of the amine. At basic pH, the polymer exists as the free base.

Particular "weakly basic groups" which can be a part of polymerizable monomers useful in this invention include, but are not limited to, cyclic amine groups, or primary, secondary or tertiary aminoalkyl groups which can be protonated at acidic pH. Useful cyclic amine groups include, but are not limited to, imidazolyl, isoxazolyl, pyridyl, piperidyl, piperazinyl, pyrazolyl, triazolyl, tetrazolyl, oxadiazolyl, pyridazinyl, pyrimidyl, pyrazinyl, quinolinyl and quinazolinyl groups. The preferred groups are cyclic groups which are aromatic, and the imidazolyl group is most preferred. Useful aminoalkyl or cyclic amine groups are linked to vinyl groups of the monomers using convenient linking groups including alkylene, amido or ester groups, and multiple alkylene groups can be linked together with imino, oxy, amide, carbonyl or ester groups.

Generally useful polymers for capturing nucleic acids are comprised of recurring units derived by addition polymerization of:

a) from about 15 to 100 weight percent of a water-soluble, weakly basic ethylenically unsaturated polymerizable monomer having at least one group which can be protonated at acidic pH and which is selected from the group consisting of aminoalkyl, imidazolyl, isoxazolyl, pyridyl, piperidyl, piperazinyl, pyrazolyl, triazolyl, tetrazolyl, oxadiazolyl, pyridazinyl, pyrimidyl, pyrazinyl, quinolinyl and quinazolinyl, b) from 0 to about 35 weight percent of a nonionic, hydrophilic ethylenically unsaturated polymerizable monomer, and c) from 0 to about 85 weight percent of a nonionic, hydrophobic ethylenically unsaturated polymerizable monomer.

Preferably, the weakly basic polymer is comprised of recurring units of from about 20 to about 100 weight percent of a), from 0 to about 25 weight percent of b), and from 0 to about 80 weight percent of c).

A more specific class of monomers useful in a) above are those represented by the structure (I):

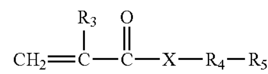

wherein $R^3$ is hydrogen or methyl, and X is oxy or imino. In addition, $R^4$ is a divalent hydrocarbon linking group having from 1 to 8 carbon and hetero atoms in the chain and comprising one or more alkylene groups (such as methylene, ethylene, n-propylene, isopropylene and n-pentylene), providing that when there is more than one alkylene group, they are linked together in $R^4$ with one or more carbonyl, oxy, imino, ester or amido groups in any operable combination. By "operable combination" is meant that those groups can be combined with the alkylene groups in any chemically possible configuration, and can be used in combination (connected to each other) in chemically possible ways (such as oxycarbonyl, carbonamido and others readily apparent to one skilled in the art). It is also to be understood that $R^4$ can be terminated (or connected to $R^5$) with a carbonyl, oxy, imino, ester or amido group.

$R^5$ is a cyclic amine or primary, secondary or tertiary aminoalkyl group, as defined above, which can be protonated at acidic pH.

Examples of useful type a) monomers include, but are not limited to, 1-vinylimidazole, 2-methyl-1-vinylimidazole, 2-vinylpyridine, 1-hydroxy-6-vinyl-1H-benzotriazole, 2-aminoethyl methacrylate hydrochloride, 2-aminoethyl acrylate hydrochloride, N-(3aminopropyl)methacrylamide, 2-vinylquinoline, N-(3imidazolylpropyl)methacrylamide, N-(2-imidazolylethyl)methacrylamide, N-(3-imidazolylpropyl)acrylamide, N-(1,1-dimethyl-3-N-imidazolylpropyl) acrylamide, N-(imidazolylmethyl)acrylamide, 1-vinylpyrrolidinone, 3-(N,N-dimethylamino)propyl metharcylate and acid addition salts of the noted free bases.

A class of novel monomers of type a) of this invention can be used to prepare either homopolymers or copolymers. These monomers are defined by the structure (II):

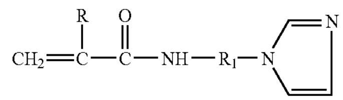

wherein R is hydrogen or methyl. Preferably, R is methyl. In addition, $R^1$ is branched or linear alkylene of 1 to 3 carbon atoms (such as methylene, ethylene, trimethylene or propylene). Preferably, $R^1$ is alkylene of 2 or 3 carbon atoms. More preferably, $R^1$ is trimethylene.

Particularly useful monomers having structure (II) include, hut are not limited to, N-(3-imidazolylpropyl)methacrylamide, N-(2-imidazolylethyl)methacrylamide, N-(3-imidazolylpropyl)acrylamide, N-(1,1-dimethyl-3-N-imidazolylpropyl)acrylamide, N-(imidazolylmethyl)acrylamide, and their acid addition salts. Of the novel monomers described herein, the first compound is most preferred.

Preferred type a) monomers include 1-vinylimidazole and N-2-methyl-1-vinylimidazole.

If the monomers of type a) have low or no water solubility, they can also be polymerized in the form of their acid addition salts (such as the hydrochloride or hydrobromide).

Monomers identified as type b) monomers are those which are defined herein as "hydrophilic", meaning those which, when homopolymerized, provide homopolymers which are water-soluble at pH 7 or above. Generally, such monomers nave hydrophilic groups such as hydroxy, amine (primary, secondary, tertiary and cyclic), amide, sulfonamide and polyethyleneoxy groups, but it is not necessary that they comprise such groups if the noted homopolymer water-solubility parameter is met.

Representative monomers of type b) include, but are not limited to, acrylamide, 2-hydroxyethyl acrylate, 2,3-dihydroxypropyl acrylate, 2,3-dihydroxypropyl methacrylate, poly(ethyleneoxy)ethyl methacrylate (having 2 to 10 ethyleneoxy groups), and N,N-dimethylacrylamide. A preferred monomer is acrylamide.

Monomers identified as type c) monomers are those which are defined herein as "hydrophobic", meaning those which, when homopolymerized, provide homopolymers which are water-insoluble at pH 7 or above, irrespective of the type of pendant groups they may possess.

Representative monomers of type c) include, but are not limited to, methacrylamide, 2-hydroxyethyl methacrylate, N-t-butylmethacrylamide, ethyl acrylate, methyl acrylate, butyl acrylate, methyl methacrylate, styrene, vinyltoluene and other vinyl aromatics and others which would be readily apparent to one skilled in the art. A preferred monomer is 2-hydroxyethyl methacrylate.

The monomers of types a), b) and c) which are not novel are generally readily available from commercial sources, or prepared using conventional procedures and starting materials.

The novel monomers of structure (II) can be prepared generally by condensation of a 1-(aminoalkyl)imidazole with a (meth)acryloyl chloride using appropriate conditions which would be readily apparent to one skilled in the art. A representative preparation of a preferred monomer is provided below preceeding the examples. More details about such monomers can be obtained from commonly assigned U.S. Pat. No. 5,434,270, Ponticello et al., entitled "Weakly Basic Polymerizable Monomers and Polymers Prepared Therefrom".

The homopolymers and copolymers described herein can be prepared using conventional solution polymerization techniques which are well known in the art, although there are certain preferred conditions which are illustrated in the preparatory methods provided below preceding the Examples. The ratio of various monomers can be adjusted, as one skilled in the art would know, to provide polymers which are either water-soluble or water-insoluble at basic pH, as long as such polymers remain water-soluble at acidic pH.

Solution polymerization generally involves dissolving the monomers in a suitable solvent (including water or various water-miscible organic solvents) and polymerizing in the presence of a suitable free radical initiator. The resulting polymer is water-soluble at acidic pH, so it is precipitated using a solvent such as acetone, purified and redissolved in water for future use.

Particularly useful polymers described herein include, but are not limited to, poly[N-(3-imidazolylpropyl)methacrylamide hydrochloride-co-acrylamide], poly[N-(3-imidazolylpropyl)methacrylamide hydrochloride-co-2-hydroxyethyl methacrylate], poly(1-vinylimidazole), poly(2-aminoethyl methacrylate hydrochloride-co-2-hydroxyethyl methacrylate), poly(1-vinylimidazole hydrochloride-co-2-hydroxyethyl methacrylate), poly[N-(1,1-dimethyl-3-imidazolylpropyl)acrylamide]poly(N-2-methyl-1-vinyl imidazole) and acid addition salts of the free base polymers.

In preferred embodiments, the polymers used are water-insoluble at basic pH. Such polymers are prepared using type a) monomers as well as type c) monomers but with limited amounts (less than 15 weight of type b) monomers to prevent solubilization of the polymer at basic pH. Representative polymers of this type include, but are not limited to, poly[N-(3-imidazolylpropyl)-methacrylamide hydrochloride-co-2-hydroxyethyl methacrylate], poly(1-vinylimidazole), poly(2-aminoethyl methacrylate hydrochloride-co-2-hydroxyethyl methacrylate) and poly(1-vinylimidazole hydrochloride-co-2-hydroxyethyl methacrylate).

The present invention is also directed to the amplification or detection of one or more specific nucleic acid sequences present in one or more target nucleic acids released as noted above. Moreover, a plurality of target nucleic acids can be amplified and detected simultaneously by using a corresponding set of primers and detection means for each specific nucleic acid. Multiple sequences in the same nucleic acid can also be amplified and detected.

A "PCR reagent" refers to any of the reagents generally considered useful in PCR, namely a set of primers for each target nucleic acid, a DNA polymerase, a DNA polymerase cofactor and two or more deoxyribonucleoside-5'-triphosphates (dNTP's).

As used herein in referring to primers or probes, the term "oligonucleotide" refers to a molecule comprised of four or more deoxyribonucleotides or ribonucleotides, and preferably more than ten. Its exact size is not critical but depends upon many factors including the ultimate use or function of the oligonucleotide. The oligonucleotide may be derived by any method known in the art.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates), a DNA polymerase and a DNA polymerase cofactor, and suitable temperature and pH. Normally, such conditions are what are known in the art as "high stringency" conditions so that nonspecific amplification is minimized. The primer must be long enough to initiate the synthesis of extension products in the presence of the DNA polymerase. The exact size of each primer will vary depending upon the use contemplated, the complexity of the targeted sequence, reaction temperature and the source of the primer. Generally, the primers used in this invention will have from 10 to 60 nucleotides.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188). Naturally occurring primers isolated from biological sources are also useful (such as restriction endonuclease digests). As used herein, the term "primer" also refers to a mixture of primers. Thus, each set of primers for a given target nucleic acid may include two or more primers for each opposing target strand.

One or both primers can be labeled with the same or different label for detection or capture of amplified product. Procedures for attaching labels and preparing primers are well known in the art, for example, as described by Agrawal et. al, Nucleic Acid Res., 14, pp. 6227-45 (1986), U.S. Pat. No. 4,914,210 (Levenson et al) relating to biotin labels, U.S. Pat. No. 4,962,029 (Levenson et al) relating to enzyme labels, and the references noted therein. Useful labels also include radioisotopes, electron-dense reagents, chromogens, fluorogens, phosphorescent moieties, ferritin and other magnetic particles (see U.S. Pat. No. 4,795,698 of Owen et al and U.S. Pat. No. 4,920,061 of Poynton et al), chemiluminescent moieties (such as luminol), and other specific binding species (avidin, streptavidin, biotin, sugars or leetins). Preferred labels are enzymes, radioisotopes and specific binding species (such as biotin). Useful enzymes include, glucose oxidase, peroxidases, uricase, alkaline phosphatase and others known in the art and can be attached to oligonucleotides using known procedures. Reagents to provide a colorimetric or chemiluminescent signal with such enzymes are well known.

Where the label is an enzyme such as a peroxidase, at some point in the assay, hydrogen peroxide and suitable dye-forming compositions are added to provide a detectable dye. For example, useful dye-providing reagents include tetramethylbenzidine and derivatives thereof, and leuco dyes, such as water-insoluble triarylimidazole leuco dyes (as described in U.S. Pat. No. 4,089,747 of Bruschi), or other compounds which react to provide a dye in the presence of peroxidase and hydrogen peroxide. Particularly useful dye-providing compositions are described in EP-A-0 308 236 (published Mar. 22, 1989). Chemiluminescent signals in response to a peroxidase label can also be generated using the appropriate reagents.

If one or both primers are biotinylated, the amplified nucleic acid can be detected using detectably labeled avidin or an equivalent thereof (such as streptavidin). For example, avidin can be conjugated with an enzyme, or have a radioisotope using known technology. Biotin on the amplified product complexes with the avidin, and appropriate detection techniques to detect a radioactive, colorimetric or chemiluminescent signal are used.

As used herein, a capture "probe" is an oligonucleotide which is substantially complementary to a nucleic acid sequence of one or more strands of the target nucleic acid, and which is used to insolubilize the amplified nucleic acid. The probe oligonucleotide is generally attached to a suitable water-insoluble substrate such as polymeric or glass beads, microtiter plate well, thin polymeric or cellulosic film or other materials readily apparent to one skilled in the art. The oligonucleotide is generally from about 12 to about 40 nucleotides in length, although the length is not critical.

A DNA polymerase is an enzyme which will add deoxynucleoside monophosphate molecules to the 3+-hydroxy end of the primer in a complex of primer and template, but this addition is in a template dependent manner (that is, dependent upon the specific nucleotides in the template). Many useful DNA polymerases are known in the art. Preferably, the polymerase is "thermostable", meaning that it is stable to heat, especially the high temperatures used for denaturation of DNA strands. More particularly, the thermostable DNA polymerases are not substantially inactivated by the high temperatures used in PCR as described herein.

A number of thermostable DNA polymerases have been reported in the art, including those mentioned in detail in U.S. Pat. No. 4,965,188 (noted above) and U.S. Pat. No. 4,889,818 (Gelfand et al), incorporated herein by reference. Particularly useful polymerases are those obtained from various *Thermus* bacterial species, such as *Thermus aquaticus, Thermus thermophilus, Thermus filiformis* or *Thermus flavus*. Other useful thermostable polymerases are obtained from a variety of other microbial sources including *Thermococcus literalis, Pyrococcus furiosus, Thermotoga* sp. and those described in WO-A-89/06691 (published Jul. 27, 1989). Some useful polymerases are commercially available. A number of techniques are known for isolating naturally-occurring polymerases from organisms, and for producing genetically engineered enzymes using recombinant techniques, as noted in the art cited in this paragraph.

A DNA polymerase cofactor refers to a nonprotein compound on which the enzyme depends for activity. A number of such materials are known cofactors including manganese and magnesium salts. Useful cofactors include, but are not limited to, manganese and magnesium chlorides, sulfates, acetates and fatty acid salts (for example, butyric, caproic, caprylic, capric and lauric acid salts). The smaller salts, that is chlorides, sulfates and acetates, are preferred.

Also needed for PCR are two or more deoxyribonucleotide-5'-triphosphates, such as dATP, dCTP, dGTP, dUTP or dTTP. Usually, dATP, dCTP, dGTP and dTTP are all used in PCR. Analogues such as dITP and 7-deaza-dGTP are also useful.

Also useful in the practice of the invention is an antibody specific to the DNA polymerase, which antibody inhibits its enzymatic activity at temperatures below about 50° C., but which antibody is deactivated at higher temperatures. Representative monoclonal antibodies having these properties are described in U.S. Pat. No. 5,338,671 (Scalice et al), incorporated herein by reference. Antibody fragments can be used in place of the whole molecule if they have equivalent properties.

The PCR reagents described herein are provided and used in PCR in suitable concentrations to provide amplification of the target nucleic acid. The minimal amounts of DNA polymerase is generally at least about 1 unit/100 μl of solution, with from about 4 to about 25 units/100 μl being preferred. A "unit" is defined herein as the amount of enzyme activity required to incorporate 10 nmoles of total nucleotides (dNTP's) into an extending nucleic acid chain in 30 minutes at 74° C. The concentration of each primer is at least about 0.075μ molar with from about 0.2 to about 1μ molar being preferred. All primers are present in about the same amount (within a variation of 10% of each). The cofactor is generally present in an amount of from about 1 to about 15 mmolar, and each dNTP is generally present at from about 0.1 to about 3.5 mmolar in the reaction mixture. As used in this paragraph, the modifier "about" refers to a variance of +/−10% of the noted value.

The PCR reagents can be supplied individually, or in a buffered solution having a pH in the range of from about 7 to about 9 using any suitable buffer.

Since the target nucleic acid to be amplified and detected is usually in double strand form, the two strands must be separated (that is, denatured) before priming can take place. This can occur during the extraction process, but preferably, it occurs in a separate step afterwards. Heating to a suitable temperature (identified as "first temperature" or $T_1$ herein) is a preferred means for denaturation. Generally, this first temperature is in the range of from about 85° to about 100° C. for a suitable time, for example from 1 to about 240 seconds (preferably 1 to about 40 seconds). This initial denaturation step can also be included in the first amplification cycle. In such instances, denaturation may be longer in the first cycle (for example, up to 240 seconds) whereas later cycles can have much shorter denaturation steps (for example, up to 30 seconds).

The denatured strands are then primed with the appropriate sets of primers by cooling the reaction mixture to a second temperature, $T_2$, which is generally within the range of from about 55° to about 70° C. It is desired that cooling is done as quickly as possible, but with presently known equipment, it generally takes place over a time period of from about 5 to about 40 seconds, and more preferably for from about 5 to about 20 seconds.

Once the denatured strands are cooled, the reaction mixture containing the PCR reagents is incubated at a third temperature, $T_3$, generally for from 1 to about 120 seconds, and preferably for from 1 to about 80 seconds, to effect formation of primer extension products. Generally, the third temperature is within the range of from about 55° to about 74° C. Preferably, it is within the range of from about 62° to about 70° C.

In a most preferred embodiment, the second and third temperatures are the same and are within the range of from about 62° to about 70° C. Thus, priming and primer extension are preferably carried out in the same step.

Thus, an amplification cycle comprises the denaturation, priming (or annealing) and primer extension steps described above. Generally, at least 15 of such amplification cycles are carried out in the practice of this invention with the maximum number of cycles being within the discretion of the particular user. In most instances, 15 to 50 amplification cycles are used in the method with 15 to 40 cycles being preferred. Each amplification cycle is generally from about 20 to about 360 seconds, with a cycle time of from about 30 to about 120 seconds being preferred and from about 30 to about 90 seconds being more preferred. However, longer or shorter cycle times can be used if desired.

When used in reference to time for a given step in the amplification procedure, the term "about" refers to +/−10% of that time limit. Moreover, when used in reference to temperatures, the term "about" refers to +/−0.5° C.

Detection of amplified products can be accomplished using any known procedure, including Southern blotting techniques, as described in U.S. Pat. No. 4,965,188 (noted above), or by use of labeled probes or primers, as is known in the art.

Alternatively to the embodiments described above, the amplified products can be detected using a labeled oligonucleotide which is complementary to one of the primer extension products.

All reagents for performing the TaqMan assay were purchased from Applied Biosystems, a Division of Perkin-Elmer Co., Foster City, Calif., including: β-Actin detection reagents (cat. no. 401846), DNA template reagents (cat. no. 401970) and TaqMan PCR Core Reagent Kit (cat. no. N808-0228). Assays were performed using the PCR Master mix and thermal cycling profiles for the β-Actin TaqMan assay provided by the manufacturer. One microliter of DNA template reagent was added to 49 μL of PCR β-Actin Master mix in an ABI Prism 7700 Sequence Detection System (Applied Biosystems) and fluorescence was measured during the 40 PCR cycles.

FIG. 1 shows a calibration curve for different starting levels of DNA versus Threshold cycle count, which is a value determined by the instrument and represents the estimated number of PCR cycles at which a preselected fluorescence signal will be obtained. Thus, the TaqMan assay for a β-Actin gene fragment provides a good analytical tool for measuring DNA concentration present in a sample.

In the examples that follow, DNA from the single copy (per cell) β-Actin gene was extracted from the indicated samples according to the method of the invention or using the indicated prior art method which utilizes a cell lysing reagent. β-Actin DNA extracted thereby was amplified using the PCR Master Mix and thermal cycling profiles and TaqMan detection as per the manufacturer's recommended procedures.

In the heterogeneous detection systems of this invention, the amplified products are captured on a water-insoluble substrate of some kind, and the other materials in the reaction mixture are removed in a suitable manner, such as by filtration, centrifugation, washing or another separation technique.

Capture probes can be attached to water-insoluble supports using known attachment techniques (including absorption and covalent reactions). One such technique is described in EP-A-0 439 222 (published Sep. 18, 1991). Other techniques are described, for example, in U.S. Pat. No. 4,713,326 (Dattagupta et al), U.S. Pat. No. 4,914,210 (Levenson et al) and EP-B-0 070 687 (published Jan. 26, 1983). Useful separation means include filtration through membranes such as polyamide microporous membranes commercially available from Pall Corporation.

However, any useful solid support can be used to anchor the capture probe and eventual hybridization product, including microtiter plates, test tubes, beakers, magnetic or polymeric particles, metals, ceramics, and glass wool to name a few. Particularly useful materials are magnetic or polymeric particles having reactive groups useful for covalently attaching the capture probe. Such particles are generally from about 0.001 to about 10μ meters. Further details about examples of such materials are provided in U.S. Pat. No. 4,997,772 (Sutton et al), U.S. Pat. No. 5,147,777 (Sutton et al), U.S. Pat. No. 5,155,166 (Danielson et al) and U.S. Pat. No. 4,795,698 (Owen et al), all incorporated herein by reference.

The capture probe can be affixed to a flat support such as a polymeric film, membranes, filter papers, or resin-coated or uncoated paper. Capture probe affixed to polymeric particles can also be immobilized on such flat supports in a suitable manner, for example, as dried deposits, or adhered by heat fusion or with adhesives. The capture probe can be affixed, for example, to a flat support in the self-contained test device of this invention. Other details of such materials are provided in EP-A-0 408 738 (published Jan. 23, 1991), WO 92/16659 (published Oct. 1, 1992) and U.S. Pat. No. 5,173,260 (Sutton et al).

The capture probes can be arranged on a suitable support in any configuration, for example rows of round deposits or stripes.

The present invention can also be used in what are known as "homogeneous" amplification procedures in which target nucleic acids are detected without the need for capture reagents. The details of such assays are known in the art, such as in EP-A-0 487 218 (published May 27, 1992) and EP-A-0 512 334 (published Nov. 11, 1992).

The amplification reaction composition can be included as one individually packaged component of a test kit useful for various amplification assays. The kit can include other reagents, solutions, equipment and instructions useful in the method of this invention, including capture reagents immobilized on a water-insoluble substrate, wash solutions, detection reagents and other materials readily apparent to one skilled in the art. In addition, the test kit can include a separately packaged weakly basic polymer as described above, buffers, weak or strong bases and other reagents needed for either or both amplification and specimen sample preparation. The test kit can also include a test device containing one or more other kit components. This test device is preferably "self-contained" as that term is understood in the art. Other kits can include the weakly basic polymer described herein and one or more reagents (such as detection or capture probes) used in hybridization assays.

The following examples are included to illustrate the practice of this invention, and are not meant to be limiting in any way. All percentages are by weight unless otherwise noted.

Materials and Methods for Examples

Preparation of N-(3-Imidazolylpropyl)-methacrylamide

This procedure shows the preparation of a novel monomer of structure (I), identified above, but the preparation is representative of how other monomers within the scope of this invention could readily be prepared.

A solvent mixture was prepared by mixing water (100 ml) containing sodium hydroxide (12.8 g, 0.32 mole) and dichloromethane (200 ml) containing 1-(3-aminopropyl) imidazole (37.5 g, 0.3 mole), and cooled in an ice bath. To this cooled mixture was added all at once, methacryloyl chloride (34.8 g, 0.3 mole) in dichloromethane (100 ml) with vigorous stirring under a nitrogen atmosphere. Heat was evolved with the temperature of the mixture rising to about 60° C., and the mixture was vigorously stirred for another 10 minutes, and then the organic layer was allowed to separate. The water layer was extracted twice with dichloromethane, (100 ml each time). The combined organic solution (the organic solvent layer and extracts) was washed with saturated sodium chloride (100 ml), dried over anhydrous sodium sulfate, filtered, and the solvent was removed. The residue was dissolved in chloroform (50 ml), followed by the addition of ethyl ether (50 ml) to the cloud point.

The resulting reaction product crystallized at about 0° C., and was filtered to give a white solid having a melting point of 45°-46° C. The yield was 70%.

Analytical data included: m/e (M-193),

1H NMR (DMSO d6) 1.8 (m,2H,C—$CH_2$—C,$CH_3$), 3.02 (m,2H,N—$CH_2$), 3.95 (t,2H, im-$CH_2$), 5.25 and 5.6 (AB, 2H,vinyl-$CH_2$), 6.82 and 7.15 (AB,2H,4,5-H of im), 7.6 (s,1H,2-H of im), 7.95 (m, 1H,NH).

Preparation of Homopolymer

A preferred homopolymer prepared from a novel monomer described herein was prepared by adding 2,2'-azobis(2-methylpropionitrile) (300 mg) to a solution of N-(3-imidazolylpropyl)methacrylamide (12.5 g, 0.065 mole) in water (90 ml) and isopropanol (10 ml), maintained under a nitrogen atmosphere. The resulting solution was heated, while being stirred, to 65°-70° C. in a water bath for 3 hours. After about 1.5 hours of that time, concentrated HCl (3 ml) was added, and the stirring was continued under nitrogen for the remaining time. The solution was then concentrated on a rotary evaporator to about 25 ml, and the resulting polymer product was precipitated in acetone (over 4 liters), filtered and dissolved in deionized water (80 ml). The solution contained 12% solids.

Preparation of First Copolymer

Poly[N-(3-imidazolylpropyl)methacrylamide hydrochloride-co-acrylamide] (90:10 weight ratio) was prepared by adding 2,2'-azobis(2-methylpropionitrile) (400 mg) to a solution of N-(3-imidazolylpropyl)methacrylamide (18 g, 0.09 mole) and acrylamide (2 g, 0.028 mole) in deionized water (120 ml) and isopropanol (15 ml), maintained under a nitrogen atmosphere. The solution was heated to 65°-70° C. with Stirring for 4 hours, followed by addition of dilute HCl to lower the pH to about 2. Stirring and heating were continued for another hour, and the solution was then allowed to reach room temperature overnight.

The solution was concentrated to about 75 ml using a rotary evaporator, and the resulting polymer was precipitated in acetone (about 4 liters), filtered and dissolved in deionized water (150 ml). Further concentration to about 125 ml was carried out to remove residual acetone. The polymer was present at 15.5% solids.

Preparation of Second Copolymer

Poly[2-aminoethyl methacrylate hydrochloride-co-2-hydroxyethyl methacrylate] (20:80 weight ratio) was prepared by adding 2,2'-azobis(2-methylpropionitrile) (400 mg) to a solution of 2-aminoethyl methacrylate hydrochloride (4 g, 0.02 mole) and 2-hydroxyethyl methacrylate (16 g, 0.12 mole) in deionized water (180 ml) and ethanol (20 ml), maintained under a nitrogen atmosphere. The solution was heated to 65°-70° C. with stirring for 4 hours. Stirring and heating were continued for another hour, and the solution was then allowed to reach room temperature overnight.

The resulting polymer was precipitated in acetone (about 4 liters), filtered and dissolved in deionized water (150 ml). Further concentration to about 125 ml was carried out to remove residual acetone. The polymer was present at 5.6% solids.

Preparation of Third Copolymer

Poly[1-vinylimidazole-co-2-hydroxyethyl methacrylate] (50:50 weight ratio) was prepared by adding 2,2'-azobis(2-methylpropionitrile) (350 mg) to a solution of 1-vinylimidazole (10 g, 0.1 mole) and 2-hydroxyethyl methacrylate (10 g, 0.077 mole) in N,N-dimethylformamide (160 ml), maintained under a nitrogen atmosphere. The solution was heated to 65°-70° C. with stirring for 7 hours.

After sitting at room temperature overnight, the polymer was precipitated in acetone (about 4 liters), filtered and dissolved in deionized water (200 ml) containing concentrated HCl (8.5 ml). Further concentration was carried out to remove residual acetone. The polymer was present at 12.4% solids.

Preparation of Fourth Copolymer

Poly(1-vinylimidazole-co-2-hydroxyethyl methacrylate) (25:75 weight ratio) was prepared in a fashion like the "Third Copolymer". The resulting solution contained 13.7% solids.

Deoxyribonucleotides (dNTP's), tris(hydroxymethyl) aminomethane buffer and lyophilized calf thumus DNA were obtained from Sigma Chemical Co.

Gel electrophoresis was carried out by adding the amplification product mixture (6.75 μl) to agarose gels (2.5%) which had been prestained with ethidium bromide (0.4 mg/ml final concentration). The gels were electrophoresed at about 8 volts/cm for about 1 hour using an electrophoresis buffer (600 ml) containing ethidium bromide (0.4 mg/ml final concentration). The buffer was a mixture of tris(hydroxymethyl)aminomethane, borate and ethylenediaminetetraacetic acid. The resulting bands were compared to conventional molecular weight markers, and the product band intensity was scored (115-mer for HIV1 and 383-mer for *M. tuberculosis*) on a 0 to 5 scale with 0 representing no detectable signal and 5 representing the highest signal.

Other reagents and materials were obtained either from commercial sources or prepared using readily available starting materials and conventional procedures.

The invention has been described in detail with particular reference to preferred embodiments thereof, but it will be understood that variations and modifications can be effected within the spirit and scope of the invention.

EXAMPLE 1—CAPTURE AND RELEASE OF DNA USING WEAKLY BASIC HOMOPOLYMER

This example illustrates the practice of the present invention to capture and release a nucleic acid using poly(1-vinylimidazole).

Various volumes of poly(1-vinylimidazole) [of a 1:10 dilution of 2.4% stock solution (pH 2.3)] were mixed with calf thymus DNA (100 μl, 0.5 μg/μl) and vortexed to form a precipitate of nucleic acid and polymer. Centrifuging for 1 minute was then carried out. An additional amount of polymer (10 μl of the 2.4% stock solution) was added to each supernatant and the resulting mixtures were vortexed and centrifuged to determine if the first precipitation was quantitative. Table I below shows the amount of polymer used and the type of precipitation observed for each sample.

TABLE I

| Polymer Volume (μl) | First Precipitation Pellet | Second Precipitation Pellet |
|---|---|---|
| 5 | Barely Visible | Large |
| 10 | Small to medium | Small |
| 25 | Large | Not visible |
| 50 | Very large | Not visible |

It was observed that precipitation occurred under acidic conditions (pH 2.3), and that 50 μl of the 1:10 dilution of polymer stock solution could be used to precipitate 100 μl of the calf thymus DNA solution (0.5 μg/μl) Sigma Chemical Co., St. Louis, Mo., in a nearly quantitative fashion. This observation was also confirmed using conventional gel electrophoretic methods.

Experiments were conducted to determine how to solubilize the precipitate, thereby releasing the nucleic acid for later use. Table II below shows the various pellet solubilization conditions attempted and the resulting pellet size. The most useful technique was the use of heat in combination with basic pH (no pellet). Conventional gel electrophoresis clearly indicated that at basic pH, the polymer and nucleic acids were present as free materials. Thus, the nucleic acids were available for later use, such as in PCR.

TABLE II

| Solubilizing Conditions | Pellet Size |
|---|---|
| 50 μl NaCl (4 molar) | None |
| 50 μl NaOH (50 mmolar) with heating at 55° C. for 5 minutes | Small |
| 50 μl NaOH (100 mmolar) with heating at 55° C. for 5 minutes | None |
| 50 μl NaOH (50 mmolar) with heating at 100° C. for 10 minutes | None |
| 50 μl NaOH (25 mmolar) with heating at 100° C. for 10 minutes | None |
| 50 μl "TE" buffer* with heating at 100° C. for 10 minutes | Large |
| 50 μl water with heating at 100° C. for 10 minutes | Large |

*"TE" buffer includes ethylenediaminetetraacetic acid (1 mmolar) in tris (hydroxymethyl))aminomethane hydrochloride buffer (10 mmolar, pH 8)

Table III below shows the affect of pH on the formation of a precipitate between the polymer (50 μl of 1:10 dilution of stock solution) and calf thymus DNA (100 μl of 0.5 μg/μl solution). Acidic pH was clearly required for effective capture of the nucleic acid by formation of a precipitate (pellet).

TABLE III

| pH | Pellet Size |
|---|---|
| 2.3 | Large |
| 3 | Large |
| 4 | Large |
| 7 | Clear, thick mass |
| 12 | Barely visible |

EXAMPLE 2—COMPARISON OF POLYMER CAPTURE OF DNA WITH AND WITHOUT A LYSING REAGENT

The amount of DNA released from white blood cells contacted with a lysing reagent (control) is compared with the amount released from cells not contacted with a lysing reagent (method of invention) but otherwise treated identically.

In this example, 10 mL of blood was drawn into a VACUTAINER CPT cell Preparation Tube (Becton Dickinson Co., Franklin Lakes, N.J.), and the white blood cells (WBC) were separated by means of centrifugation according to the manufacturer's recommended protocol. Final WBC concentration was determined to be 3.5×105/mL, based on microscopy.

Two hundred microliters of the WBC suspension was placed in each of eight 1.5 mL microcentrifuge tubes (Eppendorf North America, Inc., Madison, Wis.). The white blood cells were centrifuged, and washed 3 times with phosphate buffered saline, (PBS, 0.15 M NaCl, and 0.05 M potassium phosphate buffer, pH 7.5).

Control—Use of Lysing Reagent

For samples contacted with lysing reagent, the pellet in each of four separate tubes was treated as follows: Eighty microliters of lysis buffer (10 mM Tris HCl, pH 8.0, and 0.5% TWEEN 20) was added, followed by 10 μL of the thermostable protease Pre-Taq, (1 U/μL, Boehringer Mannheim Biochemicals, Indianapolis, Ind.), and the tubes were heated at 100° C. for 5 min. After heat treatment, 10 μl, of 250 mM NaOH was added, and the tubes were again heated at 105° C. for 10 min, followed by centrifugation at 14,000 rpm for 2 min.

Method of Invention—No Use of Lysing Reagent

Samples not contacted with lysis reagent were treated as follows: the pellet from each of four separate tubes was resuspended in 100 μL of PBS.

Samples prepared using both above-methods were processed identically: the tubes were centrifuged at 14,000 rpm for 2 min, the supernatant fluid from each tube was carefully decanted into new tubes and stored at room temperature prior to analysis. DNA content for each tube was analyzed using the TaqMan β-actin assay and an ABI Prism 7700 Sequence Detector as described above, with calibration based on DNA standards purchased from Perkin Elmer. The results are summarized in Table IV.

TABLE IV

COMPARISON OF DNA RELEASED FROM WHITE BLOOD CELLS WITH AND WITHOUT TREATMENT WITH LYSIS REAGENT

| # | Cell Treatment | DNA ng/μl | Average |
|---|---|---|---|
| 1 | control | 2.2 | 2.93 |
| 2 | control | 3.0 | |
| 3 | control | 3.6 | |
| 4 | control | 2.4 | |
| 5 | invention | 0.006 | 0.01 |
| 6 | invention | 0.016 | |
| 7 | invention | 0.011 | |
| 8 | invention | 0.007 | |

These data indicate that in the presence of lysis reagent, there is approximately a 300-fold greater amount of DNA released from the white blood cells. Since DNA released from white blood cells is not expected to harbor mutations, deletions or other specific cancer markers circulating in blood from a primary tumor, such non-target related DNA increases non-specific background, and therefore, has a deleterious effect on an assay for either free circulating DNA in body fluids based on the detection of specific alterations in DNA associated with cancer.

EXAMPLE 3—COMPARISON OF INVENTION WITH QIAGEN KIT METHOD FOR EXTRACTING DNA FROM SERUM

The following example demonstrates a comparison of the commercial Qiagen kit and the method of the present invention for extracting DNA from the same serum pool.

For the isolation of DNA from serum or plasma based on the method of the invention, all initial steps were performed on ice to minimize possible degradation of DNA by serum nucleases. ACES buffer (N-(2-acetamido)-2-aminoethanesulfonic acid) from Sigma Chemical Co., St. Louis, Mo. was prepared as a 250 mM stock solution, pH 6.8. DNA capture polymer, poly(1-vinylimidazole hydrochloride-co-2-hydroxyethylmethacrylate) at a 76:24 monomer weight ratio and at 2.4% solids, was synthesized by protocols described in U.S. Pat. No. 5,582,988. It is a random linear vinyl addition co-polymer made using conventional solution copolymerization in N,N-dimethylformamide with an azo initiator. The copolymer (or simply polymer) was mixed with an excess of water and concentrated HCl was added until a clear solution was obtained. The solution was then diafiltered.

Two hundred microliters of serum or plasma were added to a 1.5 mL microfuge-tube followed by the addition of 100 uL of the ACES buffer stock. After mixing by means of a vortex mixer, 15 uL of the aqueous capture polymer solution was added to the tube and the sample was again mixed for 5 sec. using a vortex mixer. The tube was centrifuged by means of a Eppendorf Microcentrifuge model 5415 (Brinkman Instruments, Westbury, N.Y.) at maximum speed for 2 min, and the supernatant fluid was decanted. One hundred microliters of 20 mM NaOH was added to the tube containing the pellet, and the tube was mixed by means of a Vortex mixer, followed by heating at 100° C. for 5 min. Samples were either maintained at 4° C. and assayed immediately following extraction or stored frozen prior to use.

For comparison, DNA was also extracted from serum or plasma using a QIAmp Blood Kit (cat 29104) from Qiagen Corp., Chatsworth, Calif. according to the manufacturer's recommended procedure. Buffers AL, AW and AE were provided in the kit. Two hundred microliters of serum were combined with 200 uL of 0.05M potassium phosphate buffer, pH 7.5, and 200 uL of Buffer AL and 25 uL of Proteinase K solution (lysing reagent) provided in the kit and the contents were immediately mixed for 15 seconds using a vortex mixer. Following incubation at 70° C. for 10 min, 210 uL of ethanol was added, and the sample was again mixed using the vortex mixer. DNA was extracted by means of a QIAamp spin column into a 2 mL collection tube. After applying the sample, the tube was centrifuged at 6,000×g for 1 min. The tube containing the filtrate was discarded. Five hundred microliters of Buffer AW was added, and the column was again centrifuged for 1 min, and the tube containing the filtrate was discarded. The column was washed an additional time with buffer AW and DNA was then eluted from the column with 200 uL of Buffer AE or distilled water preheated to 70° C. After addition of the buffer or water, the tube was incubated at room temperature for 1 min and then centrifuged at 6,000×g for 1 min.

A comparison of the steps in the Quiagen kit method and the method of the present invention are shown in Table V. The Quiagen kit requires at least 8 steps as compared with the method of the invention, which requires 3 steps.

TABLE V

COMPARISON OF STEPS INVOLVED IN DNA EXTRACTION USING THE METHOD OF THE INVENTION AND QIAGEN METHOD

IzMn (76/24)

| Polymer Capture | QIAGEN Kit |
|---|---|
| 1 ACES Buffer addition | 1 PBS buffer addition |
| 2 Polymer addition | 2 QIAGEN Protease Treatment |
| 3 DNA release by NaOH | 3 Incubation at 70° C. for 10 min. |
| | 4 Ethanol addition |
| | 5 Load QIAamp spin column and spin |
| | 6 Buffer wash the column, 1 min spin |
| | 7 Buffer wash the column, 3 min spin |
| | 8 Buffer elute the column |

A comparison of amplifiable β-actin DNA as measured by the TaqMan β-actin protocol (8 replicates) is shown in Table VI and indicates a 58% improvement in recoverable amplifiable DNA using the method of the invention (60.6 ng/mL serum) as compared to the Quiagen method (25.3 ng/mL serum).

TABLE VI

COMPARISON OF β-ACTIN DNA EXTRACTION USING THE METHOD OF THE INVENTION AND QIAGEN METHOD

| Sample # | DNA Prep | Serum Vol (μl) | DNA ng/μ | AVEG | SDTEV | ngDNA/μl serum | ngDNA/ml serum |
|---|---|---|---|---|---|---|---|
| 1 | Polymer | 200 | 0.038 | 0.060625 | 0.016475 | 0.0606 | 60.63 |
| 2 | Polymer | 200 | 0.06 | | | | |
| 3 | Polymer | 200 | 0.06 | | | | |
| 4 | Polymer | 200 | 0.095 | | | | |
| 5 | Polymer | 200 | 0.051 | | | | |
| 6 | Polymer | 200 | 0.06 | | | | |
| 7 | Polymer | 200 | 0.068 | | | | |
| 8 | Polymer | 200 | 0.053 | | | | |
| 1 | QIAGEN | 200 | 0.032 | 0.02525 | 0.014945 | 0.0253 | 25.25 |
| 2 | QIAGEN | 200 | 0.013 | | | | |
| 3 | QIAGEN | 200 | 0.022 | | | | |
| 4 | QIAGEN | 200 | 0.025 | | | | |
| 5 | QIAGEN | 200 | 0.059 | | | | |
| 6 | QIAGEN | 200 | 0.016 | | | | |
| 7 | QIAGEN | 200 | 0.015 | | | | |
| 8 | QIAGEN | 200 | 0.02 | | | | |

EXAMPLE 4—RECOVERY OF β-ACTIN DNA FROM SERUM OF INDIVIDUALS DIAGNOSED WITH PANCREATIC CANCER AND CONTROLS USING THE METHOD OF THE INVENTION

This example provides the results of experiments providing a quantitative measure of the amount of β-Actin DNA recovered from the serum of normal and pancreatic cancer patients using the method of the invention in accordance with the materials and procedures of Example 8 herein. β-Actin DNA so recovered from each sample was quantified using the TaqMan β-actin protocol described earlier.

As shown in Table VII, using the method of the invention a total of 8 replicates from the same human serum pool yielded an average of 12 ng of β-Actin DNA/mL of serum, whereas β-Actin DNA in the serum of 10 different pancreatic cancer patients recovered using the method of the invention was greatly elevated (average=146 ng/mL). These findings of elevated β-Actin DNA in the serum of individuals having pancreatic cancer as compared with that of normals are supported by several reports in the literature (4,9).

TABLE VII

β-ACTIN DNA EXTRACTION FROM NORMAL SERUM POOL AND SERUM FROM INDIVIDUALS AFFLICTED WITH PANCREATIC CANCER USING THE METHOD OF THE INVENTION

| Sample # | Sample source 300 μl | Quantity ng/μl | AVEG | SDTEV | ngDNA/ μl in serum | ngDNA/ ml in serum |
|---|---|---|---|---|---|---|
| 1 | Human Serum Pool | 0.045 | 0.072875 | 0.049453 | 0.0121 | 12 |
| 2 | | 0.056 | | | | |
| 3 | | 0.19 | | | | |
| 4 | | 0.056 | | | | |
| 5 | | 0.072 | | | | |
| 6 | | 0.032 | | | | |
| 7 | | 0.078 | | | | |
| 8 | | 0.054 | | | | |
| 1 | Pancreatic Cancer Patient Serum | 1 | 0.881875 | 1.07686 | 0.1470 | 146 |
| 2 | | 0.33 | | | | |
| 3 | | 0.16 | | | | |
| 4 | | 0.88 | | | | |
| 5 | | 0.69 | | | | |
| 6 | | 0.075 | | | | |
| 7 | | 0.32 | | | | |
| 8 | | 0.43 | | | | |
| 9 | | 3.4 | | | | |
| 10 | | 1.1 | | | | |

EXAMPLE 5—COMPARISON OF THE METHOD OF THE INVENTION AND QIAGEN METHOD FOR RECOVERY OF β-ACTIN DNA FROM SERUM OF INDIVIDUALS DIAGNOSED WITH PANCREATIC CANCER

In this example, β-Actin DNA recovery from 6 patients with confirmed pancreatic cancer was compared using the method of the invention and the Qiagen method in accordance with the materials and procedures of Example 3 herein. In general, as shown in Table VIII, the method of the invention yielded either higher or comparable levels of β-Actin DNA as assayed by the TaqMan β-Actin assay. Depending upon the sample, measurable DNA concentrations ranged from 31 to 310 ng/mL.

TABLE VIII

COMPARISON OF β-ACTIN DNA EXTRACTION FROM SERUM OF INDIVIDUALS AFFLICTED WITH PANCREATIC CANCER USING THE METHOD OF THE INVENTION AND QIAGEN METHOD

| Sample # | Method | ng DNA/mL serum |
|---|---|---|
| 1 | Qiagen | 263 |
| 1 | Polymer Capture | 260 |
| 2 | Qiagen | 95 |
| 2 | Polymer Capture | 102 |
| 3 | Qiagen | 88 |
| 3 | Polymer Capture | 235 |
| 4 | Qiagen | 310 |
| 4 | Polymer Capture | 275 |
| 5 | Qiagen | 31 |
| 5 | Polymer Capture | 38 |
| 6 | Qiagen | 57 |
| 6 | Polymer Capture | 65 |

Results are the average of 4 replicates per sample, except for sample 1 and 2 which are the average of 6 replicates. Sample 2 evaluated with the Qiagen protocol is the average of 2 replicates.

EXAMPLE 6—ISOLATION OF CIRCULATING DNA FROM SERUM OF NORMAL AND CANCER PATIENTS USING THE METHOD OF THE INVENTION

This example illustrates the utility of the method of the invention for isolating circulating DNA from serum of 20 normals and 30 individuals having a confirmed cancer diagnosis. Cancer patient sera included 10 confirmed pancreatic cancer patients, and 20 colon cancer samples (8 Dukes B, 5 Dukes C, and 7 Dukes D). The DNA was isolated according to the method of the invention as in the procedure described in Example 2 herein. DNA was quantified using the TaqMan β-actin assay. Polymer capture without use of a lysing reagent enabled circulating DNA to be concentrated with minimal or no contamination with DNA from undesirable cell lysis and removal of PCR interferences that may be present in serum. DNA in each serum was quantified by means of the TaqMan assay for the β-actin gene using the standard curve shown herein in FIG. 1.

The results of analyses for free circulating DNA in each sample are shown in Tables IX A and IX B and indicate that DNA levels are elevated in serum from cancer patients compared with the serum from normal individuals.

TABLE IX A

DNA CONTENT IN THE SERUM OF CANCER PATIENTS

| # | D.S. support # | Diagnosis | DNA ng/μl | ng/ml | Average ng/ml |
|---|---|---|---|---|---|
| 1 | 139980708 | Pancreatic | 0.035 | 17.5 | 26.4 |
| 2 | 310980084 | Pancreatic | 0.024 | 12 | |
| 3 | 310980107 | Pancreatic | 0.02 | 10 | |
| 4 | 310980130 | Pancreatic | 0.017 | 8.5 | |
| 5 | 310980153 | Pancreatic | 0.029 | 14.5 | |

TABLE IX A-continued

DNA CONTENT IN THE SERUM OF CANCER PATIENTS

| # | D.S. support # | Diagnosis | DNA ng/μl | ng/ml | Average ng/ml |
|---|---|---|---|---|---|
| 6 | 310980176 | Pancreatic | 0.037 | 18.5 | |
| 7 | 1111980333 | Pancreatic | 0.22 | 110 | |
| 8 | 2510980006 | Pancreatic | 0.043 | 21.5 | |
| 9 | 2510980012 | Pancreatic | 0.054 | 27 | |
| 10 | 2510980017 | Pancreatic | 0.049 | 24.5 | |
| 11 | 139980709 | Dukes B | 0.17 | 85 | 135.5 |
| 12 | 1110980326 | Dukes B | 0.14 | 70 | |
| 13 | 1110980328 | Dukes B | 0.1 | 50 | |
| 14 | 1110980332 | Dukes B | 0.11 | 55 | |
| 15 | 2410980054 | Dukes B | 0.03 | 15 | |
| 16 | 2410980059 | Dukes B | 0.048 | 24 | |
| 17 | 2611980009 | Dukes B | 1.4 | 700 | |
| 18 | 2611980018 | Dukes B | 0.17 | 85 | |
| 19 | 139980701 | Dukes C | 0.011 | 5.5 | 100.13 |
| 20 | 1110980312 | Dukes C | 0.21 | 105 | |
| 21 | 1110980319 | Dukes C | 0.39 | 195 | |
| 22 | 1110980324 | Dukes C | 0.19 | 95 | |
| 23 | 2411980086 | Dukes C | N.D. | N.D. | |
| 24 | 310980121 | Dukes D | 0.05 | 25 | 66.08 |
| 25 | 310980144 | Dukes D | 0.055 | 27.5 | |
| 26 | 310980190 | Dukes D | 0.051 | 25.5 | |
| 27 | 2411980074 | Dukes D | 0.057 | 28.5 | |
| 28 | 2611980003 | Dukes D | 0.093 | 46.5 | |
| 29 | 2611980004 | Dukes D | 0.05 | 25 | |
| 30 | 2611980012 | Dukes D | 0.61 | 305 | |

TABLE IX B

DNA CONTENT IN SERUM OF NORMALS

| # | Unit # | DNA ng/2μl | ng/ml |
|---|---|---|---|
| 1 | M58234 | ND* | ND |
| 2 | M58088 | ND | ND |
| 3 | M58089 | 0.0510 | 6.38 |
| 4 | M58090 | ND | ND |
| 5 | M58091 | ND | ND |
| 6 | M58092 | 0.0300 | 3.75 |
| 7 | M58093 | ND | ND |
| 8 | M58094 | 0.0190 | 2.38 |
| 9* | M58095 | 0.0360 | 4.50 |
| 10 | M58111 | 0.0400 | 5.00 |
| 11 | M58112 | 0.0370 | 4.63 |
| 12 | M58113 | ND | ND |
| 13 | M58115 | 0.0310 | 3.88 |
| 14 | M58116 | ND | ND |
| 15 | M58118 | 0.0230 | 2.88 |
| 16 | M58120 | 0.1200 | 15.00 |
| 17 | M58121 | 0.0390 | 4.88 |
| 18 | M58124 | 0.0190 | 2.38 |
| 19 | M58126 | 0.0590 | 7.38 |
| 20* | M58128 | 0.0290 | 3.63 |

*ND = below detection limit

EXAMPLE 7—DETECTION OF K-RAS MUTATIONS IN THE SERUM OF PANCREATIC CANCER PATIENTS

In this example, an embodiment of the invention involving polymer capture of DNA from the serum of pancreatic cancer patients was employed. Restriction endonuclease mediated selective PCR (REMS PCR) was performed (Roberts, N. J. et al., 1999, BioTechniques 27:(3)418-422, Ward, R. et al., 1998, Am. J. Pathol. 153(2):373-379, and WO96/32500) followed by gel analysis was used to detect the presence of a K-ras mutation at codon 12 (K12-ras).

Serum or plasma (300 uL) from each of 3 pancreatic cancer patients was added to separate microfuge tubes, followed by addition of 100 uL of 250 mM ACES (N-(2-Acetamido)-2-aminoethanesulfonic acid) buffer (pH 6.8 at 23° C.). Fifteen microliters (15 uL) of polymer poly (1-vinylimidazole-co-2-hydroxyethyl methycrylate (weight ratio 77/23) was added (see U.S. Pat. Nos. 5,434,270; 5,523,368. and 5,582,988) and the tubes were mixed by means of a Mini Vortexer (VWR Scientific, Rochester, N.Y.) for 10 seconds. The tubes were then centrifuged in an Eppendorf Microcentrifuge, Model 5415, at maximum speed for 2 min. The supernatant fluid was decanted and 100 uL of 20 mM sodium hydroxide was added to each tube, and the pellet was resuspended by mixing and heated to 100° C. for 10 min.

Each PCR admixture contained three sets of primers. The diagnostic primers induce a Bstn1 restriction site in wild-type ras, but not in a mutation at ras codon 12. Thus, ras wild-type DNA is selectively cleaved during PCR thermocycling, and mutant sequences of ras at codon 12 are enriched. The PCR control primer pair is used to confirm that PCR amplifiable DNA has been extracted, and the enzyme control primer pair confirms that the restriction enzyme functioned during thermocycling. Reaction admixtures contained 12 units/100 RL of recombinant Taq polymerase, and a 5-fold excess by weight (0.842 FLL) of Taq inhibiting antibody TP4-9.2 (see U.S. Pat. Nos. 5,338,671 and 5,587,287) over the polymerase, 1 mM HT50 buffer (100 mM sodium chloride, and 50 mM Tris (tris(hydroxymethyl)amino methane), pH 8.3, 0.3 ELM of diagnostic primers (see below), 5K15S (SEQ ID: NO 1) and 5K37 (SEQ ID: NO 2), 0.05 pM of PCR control primer pairs, 3K42 (SEQ ID: NO 3) and 5BK5 (SEQ ID: NO 4), 0.1~LM of enzyme control primer pairs, 5N12A (SEQ ID: NO 5) and 3N13A (SEQ ID: NO 6), 0.2 mM total dinucleoside triphosphates (dNTPs), 0.3 units/~LL of Bsll (New England BioLabs, Beverly Mass.), 1 mm dithiothreitol (DTT), 5 mM magnesium chloride, sample (typically 3~tL) and deionized water up to a final volume of 100 gL. The Taq poymerase and anti-Taq antibodies were combined and incubated for 10-15 minutes prior to the addition of the other PCR components. Thermocycling parameters were as follows: 1 cycle at 94° C. for 100 sec., and 36 cycles at 92° C. for 15 sec, and 60° C. for 60 sec. The primer sequences are as follows:

The invention claimed is:

1. A method for isolating a free circulating, extracellular nucleic acid from a mammalian species sample not previously treated with a cell lysing reagent, wherein said method comprises the steps of:

A) admixed in buffer at a pH of less than 7, contacting a sample suspected of containing a nucleic acid with a water-soluble, weakly basic polymer derived by addition polymerization of:

1) from about 15 to 100 weight percent of a water-soluble, weakly basic ethylenically unsaturated polymerizable monomer having at least one group which can be protonated at acidic pH and which is selected from the group consisting of aminoalkyl, imidazolyl, isoxazolyl, pyridyl, piperidyl, piperazinyl, pyrazolyl, triazolyl, tetrazolyl, oxadiazolyl, pryidazinyl, pyrimidyl, pyrazinyl, quinolinyl and quinazolinyl, 2) from 0 to about 35 weight percent of a nonionic, hydrophilic ethylenically unsaturated polymerizable monomer, and 3) from 0 to about 85 weight percent of a nonionic, hydrophobic ethylenically unsaturated polymerizable monomer in an amount sufficient to form a water-insoluble precipitate of said weakly basic polymer with all nucleic acids present in said lysate, B) separating said water-insoluble precipitate from said sample, and C) contacting said precipitate with a base to raise the buffer pH to greater than 7, and thereby releasing said free circulating, extracellular nucleic acids from said weakly basic polymer, said weakly basic polymer derived by addition polymerization of one or more ethylenically unsaturated polymerizable monomers having an amine group which can be protonated at acidic pH.

2. The method of claim 1 further comprising the step:

D) adjusting the pH of said solution containing said released nucleic acids to from about 6 to about 9.

3. The method of claim 1 wherein said base is sodium hydroxide, potassium hydroxide, ammonium hydroxide, lithium hydroxide, sodium carbonate, sodium bicarbonate, a tertiary amine or tris(hydroxymethyl)-aminomethane.

4. The method of claim 1 wherein said weakly basic polymer is used in step A) in an amount of from about 0.01 to about 0.5 weight %.

5. The method of claim 1 wherein a weak base is used in step C), accompanied by heating said water-insoluble precipitate at from about 50° to about 125° C.

6. The method of claim 1 wherein a strong base is used in step C) without heating said water-insoluble precipitate.

* * * * *

UNITED STATES PATENT AND TRADEMARK OFFICE

CERTIFICATE OF CORRECTION

PATENT NO. : 7,262,006 B1
APPLICATION NO. : 10/019514
DATED : August 28, 2007
INVENTOR(S) : Robert T. Belly and Jianbo Sun It is certified that error appears in the above-identified patent and that said Letters Patent is hereby corrected as shown below:

Column 27,

Line 40 Claim 1, please delete “lysate”, and insert --sample--.

Signed and Sealed this

Third Day of November, 2009

David J. Kappos
*Director of the United States Patent and Trademark Office*